United States Patent [19]

Mohr et al.

[11] 4,423,226
[45] Dec. 27, 1983

[54] ZINC CHLORIDE COMPLEX COMPOUNDS

[75] Inventors: Reinhard Mohr, Offenbach am Main; Rudolf Neeb, Obertshausen, both of Fed. Rep. of Germany

[73] Assignee: Hoechst Aktiengesellschaft, Fed. Rep. of Germany

[21] Appl. No.: 243,876

[22] Filed: Mar. 16, 1981

[30] Foreign Application Priority Data

Mar. 22, 1980 [DE] Fed. Rep. of Germany ....... 3011154

[51] Int. Cl.$^3$ ...................... C07D 209/82; C07F 3/06
[52] U.S. Cl. ............................... 548/402; 260/429.9; 544/103
[58] Field of Search ...................... 544/103; 564/271; 260/429.9; 548/402

[56] References Cited

U.S. PATENT DOCUMENTS 3,894,012  7/1975  Baumann et al. .................. 544/103

FOREIGN PATENT DOCUMENTS 5451  11/1979  European Pat. Off. .

OTHER PUBLICATIONS

Chem. Abs. 79:5096b (1973).
Ullmanns Encyklopaedie der Technischen Chemie, 4th edition, vol. 8, Verlag Chemie, 1974, pp. 224 and 234–237.
Ullmanns Encyklopaedie der Technischen Chemie, 3rd edition, vol. 13, Urban & Schwarzenberg, 1962, pp. 56 and 57.

Primary Examiner—Dolph H. Torrence
Attorney, Agent, or Firm—Connolly and Hutz

[57] ABSTRACT

Zinc chloride complex compounds to which the structure of the general formula (1)

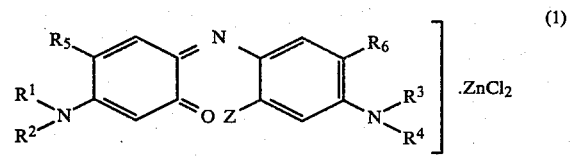

can be assigned, in which the individual radicals in the formula have the following meanings: Rhu 1 is a hydrogen atom or an optionally substituted lower alkyl group; $R^2$ is a hydrogen atom, an optionally substituted lower alkyl group or an optionally substituted phenyl radical; $R^3$ is a hydrogen atom or an optionally substituted lower alkyl group; $R^4$ is a hydrogen atom, an optionally substituted lower alkyl group or an optionally substituted phenyl radical; $R^5$ is a hydrogen atom or a halogen atom or a lower alkyl group or a lower alkoxy group, or $R^1$ and $R^5$ together form the o-phenylene radical; $R^6$ is a hydrogen atom or a halogen atom or a lower alkyl group or a lower alkoxy group; Z is a hydrogen atom or a halogen atom or a lower alkyl group or a cyano, carboxylic acid, carbamoyl or sulfamoyl group or a carbamoyl or sulfamoyl group which is monosubstituted or disubstituted by lower alkyl, or a trifluoromethyl or lower carbalkoxy group, a lower alkoxy group which can be substituted by cyano, an acyloxy group, an acylamino group, a lower alkylamino group or a lower dialkylamino group. They are prepared by reacting a nitroso compound of the formula (2)

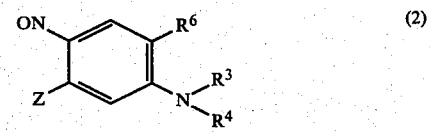

in which $R^3$, $R^4$, $R^6$ and Z have the meanings mentioned above, with an m-aminophenol of the formula (3)

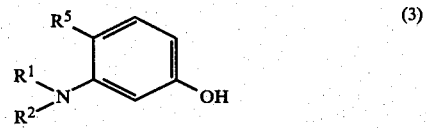

in which $R^1$, $R^2$ and $R^5$ have the meanings mentioned above, in the presence of zinc chloride and in the absence of a base. The zinc chloride complex compounds of the formula (1) can be converted by eliminating the radical Z in the formula or by removing, by oxidative means, this radical Z, in the formula, which is in the ortho-position in relation to the nitrogen atom, or the other hydrogen atom which is in the ortho-position, into the phenoxazine dyestuffs of the formula (4)

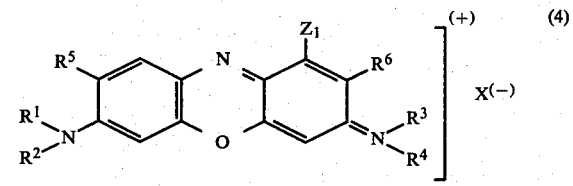

in which $R^1$, $R^2$, $R^3$, $R^4$, $R^5$ and $R^6$ have the meanings mentioned above and $Z_1$ denotes a halogen atom, a lower alkyl group, a cyano, carboxylic acid, carbamoyl or sulfamoyl group, a carbamoyl or sulfamoyl group which is monosubstituted or disubstituted by lower alkyl, or a trifluoromethyl or lower carbalkoxy group or a hydrogen atom and $X^{(-)}$ represents and anion.

1 Claim, No Drawings

ZINC CHLORIDE COMPLEX COMPOUNDS

The present invention relates to the technical field of intermediate products for dyestuffs.

European Offenlegungsschrift No. 0,005,451 has disclosed the preparation of quinoidal heavy metal complex compounds by reacting nitrosation products of oxethylated m-aminophenols with an m-aminophenol in the presence of heavy metal salts and optionally in a mixture with a basic metal salt. These heavy metal complex compounds can be converted into phenoxazine compounds by being dissolved in a neutral or alkaline, aqueous medium.

It has now been found that it is not necessary to use oxethylated nitroso-m-aminophenols as a starting material for the preparation of such intermediate products.

The present invention relates to new zinc chloride complex compounds to which the structure of the general formula (1)

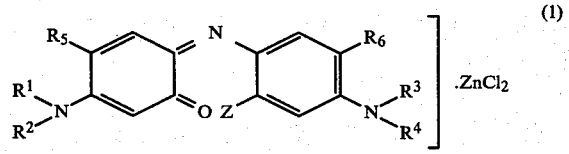

can be assigned. In this general formula (1), the terms have the following meanings: $R^1$ is a hydrogen atom or a lower alkyl group which can be substituted, for example by chlorine, by a hydroxy, lower alkoxy, cyano or lower alkanoyloxy group, such as an acetoxy group, by a carbamoyl group or by a phenyl radical; $R^2$ is a hydrogen atom or a lower alkyl group which can be substituted, for example by chlorine, by a hydroxy, lower alkoxy, cyano or lower alkanoyloxy group, such as an acetoxy group, by a carbamoyl group or by a phenyl radical, or is a phenyl radical which can be substituted, for example by substituents belonging to the group comprising chlorine, lower alkyl, lower alkoxy, carbamoyl and sulfamoyl, and sulfamoyl and carbamoyl, each of which is monosubstituted or disubstituted by lower alkyl; $R^3$ is a hydrogen atom or a lower alkyl group which can be substituted, for example by chlorine, by a hydroxy, lower alkoxy, cyano or lower alkanoyloxy group, such as an acetoxy group, by a carbamoyl group or by a phenyl radical; $R^4$ is a hydrogen atom or a lower alkyl group which can be substituted, for example by chlorine, by a hydroxy, lower alkoxy, cyano or lower alkanoyloxy group, such as an acetoxy group, by a carbamoyl group or by a phenyl radical, or is a phenyl radical which can be substituted, for example by substituents belonging to the group comprising chlorine, lower alkyl, lower alkoxy, carbamoyl and sulfamoyl, and sulfamoyl and carbamoyl, each of which is monosubstituted or disubstituted by lower alkyl; $R^5$ is a hydrogen atom, a halogen atom, such as a chlorine atom or a bromine atom, a lower alkyl group or a lower alkoxy group, or $R^1$ and $R^5$ together form the o-phenylene radical; $R^6$ is a hydrogen atom, a halogen atom, such as a chlorine or bromine atom, a lower alkyl group or a lower alkoxy group; Z is a hydrogen atom, a halogen atom, such as a chlorine atom, a lower alkyl group, a cyano, carboxylic acid, carbamoyl or sulfamoyl group, a carbamoyl or sulfamoyl group each of which is mono- or disubstituted by lower alkyl, or is a trifluoromethyl or lower carbalkoxy group, a lower alkoxy group which can be substituted by a cyano group, or is an acyloxy group, an acylamino group, a lower alkylamino group or a lower dialkylamino group.

The term "lower" in the preceding or following text is preferably understood to mean radicals or compounds in which the alkyl radical contains in each case 1 to 4 C atoms. The acyl radicals in the acyloxy and acylamino groups mentioned above are acyl radicals of aliphatic carboxylic acids having 1 to 5 C atoms, such as, for example, propionic acid or acetic acid, or of an aromatic carboxylic acid, such as benzoic acid, or of an aromatic sulfonic acid, such as benzenesulfonic acid or toluenesulfonic acid. Lower alkyl groups are preferably the methyl group and the ethyl group; lower alkoxy groups are preferably the methoxy group and the ethoxy group. Lower carbalkoxy groups are preferably the carbomethoxy group and the carboethoxy group.

The present invention also relates to a process for the preparation of the compounds defined and mentioned above, corresponding to the general formula (1), which process is characterized in that a nitroso compound of the general formula (2)

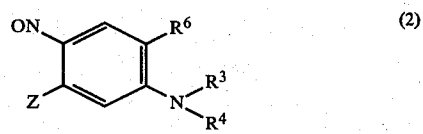

in which $R^3$, $R^4$, $R^6$ and Z have the abovementioned meanings, is reacted with an m-aminophenol of the general formula (3)

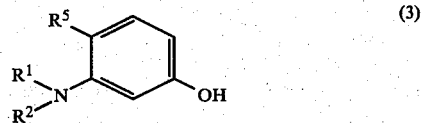

in which $R^1$, $R^2$ and $R^5$ have the abovementioned meanings, in the presence of zinc chloride and in the absence of a base. The reactants, that is to say the compounds of the formula (2) and formula (3) and zinc chloride, are employed in equimolar amounts; the zinc chloride can also be used in an excess, such as, for example, an excess of up to 1.5-molar, preferably up to 1.2-molar. Similarly, the aminophenol of the formula (3) can be employed in an excess of up to 1.1-molar.

As a rule, the nitroso compound of the general formula (2) is employed in the form of the free base, advantageously in the form of the zinc chloride complex compound.

The reactants are reacted in a protic or aprotic, polar solvent or diluent. Solvents or diluents of this type are water and aqueous solutions of electrolytes, such as sodium chloride, potassium chloride or sodium sulfate, and also customary protic or aprotic, polar organic solvents and diluents, preferably those which can be regenerated easily and without pollution of effluents. Organic, polar solvents or diluents which are particular preferred are those which are partially or completely miscible with water, such as lower alkanols, lower alkane glycols or lower alkyl ethers thereof, such as, for example, methanol, ethanol, isopropanol, butanol, ethylene glycol, ethylene glycol monomethyl ether, or ethylene glycol monoethyl ether. In certain cases, which can easily be determined by means of a laboratory test, it is, however, also possible to use as solvent or diluent formamide, dimethylformamide, dimethyl sulfoxide, N-methylpyrrolidone, dioxane, pyridine, acetonitrile, ethyl acetate, chloroform or chlorobenzene, and also, of course, mixtures of two or more of all these solvents and diluents which have been mentioned. Provided that the solvents or diluents mentioned above are miscible with water, mixtures of these solvents and diluents with water can also be used as the reaction medium.

The reaction according to the invention can be carried out at a temperature between 15° C. and 150° C.; it is preferable to carry out the reaction at a temperature between 55° and 95° C. As a result of presence of the zinc chloride, the reaction takes place in a slightly acid medium. If water is present as the reaction medium, the reaction accordingly takes place at a pH value of about 3.5 to 7.

The formation of the compounds of the general formula (1) proceeds rapidly and with evolution of heat and is complete within a few minutes at about 80° C. As a rule, the deeply colored compounds of the general formula (1) are, at least at room temperature, only slightly or very sparingly soluble in the abovementioned solvents or diluents, so that they separate out virtually analytically pure, in a well-crystallized form and in high yields.

The m-aminophenols of the general formula (3) which are used as reactants, should appropriately be partially or completely soluble in the solvent or diluent used, so that, in respect of these compounds, the reaction medium is a solution, a fine dispersion or suspension or a mixture of these forms.

The zinc chloride can be employed in the reaction mixture as the anhydrous salt or in the form of a solution. Solutions of zinc chloride which are preferably employed are concentrated aqueous solutions, such as, for example, aqueous solutions of a strength of about 40 to 65% by weight.

The nitroso compounds of the general formula (2), which, like the compounds of the general formula (3), are intermediate products which have been known and customary for a long time, can be prepared in a customary manner by introducing the nitroso group into the corresponding m-substituted aniline derivatives. These procedures are described in large numbers in the literature. The compounds of the general formula (2) are preferably employed in the reaction either in the form of the free base or particularly, however, in the form of the zinc chloride salt thereof, preferably in the form of a solution or suspension in the solvents or diluents or mixtures thereof mentioned above. The isolation of the nitroso compound of the general formula (2), particularly in a dry form, can appropriately be omitted and it is possible to use as the starting materials the solutions or suspensions of the nitroso compounds, such as are produced in the nitrosation reaction, such as, for example, the solution or suspension of the hydrochloride of the nitroso compound in water or in an aqueous solution of electrolyte. This hydrochloric acid solution can be converted into the free nitroso base by means of an agent having a basic reaction, such as an alkali metal hydroxide or carbonate or ammonia, for example by means of an aqueous sodium hydroxide solution or an aqueous solution of ammonia. However, it is preferable to use the zinc salt of this nitroso compound as the starting material. This salt can be prepared, for example, by rendering the acid solution or suspension of the nitroso compound mentioned above distinctly alkaline, for example to a pH value of 9 to 10, with aqueous sodium hydroxide or aqueous ammonia solution, and then combining the solution with an aqueous zinc chloride solution. The solution, or as a rule, suspension, of the zinc chloride salt of the nitroso compound of the general formula (2), thus obtainable, can be directly employed in the reaction with the aminophenol of the general formula (3) without the necessity of first isolating this zinc chloride salt of the nitroso compound as a reactant.

A preferred embodiment is, therefore, the reaction of the zinc chloride salts of the nitroso compound of the general formula (2) with an aminophenol of the general formula (3), preferably in equimolar amounts, using the abovementioned solvents or diluents or mixtures thereof as the reaction medium.

Preferably, the nitroso compound, dissolved or suspended in one of the abovementioned solvents or diluents or mixtures thereof, is added to the aminophenol, which is partially or completely dissolved in such a solvent or diluent or mixture thereof, and the zinc chloride, as the third reactant, can either be present in the solution or suspension of the nitroso compound or in the solution (or solution and suspension) of the aminophenol or in both.

The process according to the invention is also effected in a particularly simple manner if a nitroso compound of the general formula (2), for example in a dry form, is reacted with an aminophenol compound of the general formula (3) and anhydrous zinc chloride in an equimolar ratio or a virtually equimolar ratio in the said solvents or diluents, such as, preferably, lower alkanols or ethylene glycol or lower alkyl ethers thereof, at a temperature of up to preferably 95° C., for example at 70° to 90° C., and preferably while stirring. The zinc chloride complex formed is soon precipitated in a crystalline form. After a brief time, no further nitroso compound can be detected by thin layer chromatography. The reaction mixture is then cooled and the precipitate is isolated; the yield is virtually quantitative.

Of the above solvents or diluents, it is preferable to use methanol, ethanol, ethylene glycol, ethylene glycol monomethyl ether or ethylene glycol monoethyl ether and isopropanol or mixtures thereof, and also these solvents or diluents in the form of mixtures with water.

The compounds of the general formula (1) precipitated at the end of the reaction are filtered off and, if appropriate, washed with water or an aqueous solution of electrolyte or with one of the other abovementioned diluents or solvents or mixtures thereof in which the substance is sparingly soluble. The yield is virtually quantitative and the products are very pure.

The compounds of the general formula (1), i.e. the zinc chloride complex compounds obtainable in accordance with the process of the invention by reacting the compounds of the general formula (2) with the compounds of the general formula (3) and zinc chloride, are valuable intermediate products; they can be used for the preparation of phenoxazine compounds (dyestuffs). The present invention also relates, therefore, to the use of the compounds of the general formula (1), i.e. of these zinc chloride complex compounds which can be obtained in accordance with the invention, as intermediate products for the preparation of phenoxazine compounds of the general formula (4)

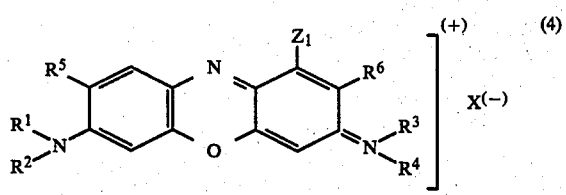

in which $R^1$, $R^2$, $R^3$, $R^4$, $R^5$ and $R^6$ have the abovementioned meanings, $Z_1$ denotes a halogen atom, a lower alkyl group, a cyano group, a carboxylic acid group, a carbamoyl group, a sulfamoyl group, a carbamoyl or sulfamoyl group, each of which is monosubstituted or disubstituted by lower alkyl, a trifluoromethyl group or a lower carbalkoxy group, or preferably a hydrogen atom, and $X^{(-)}$ represents an anion, i.e. relates to a process for the preparation of these phenoxazine compounds of the general formula (4) by cyclizing the zinc chloride complex compounds according to the invention, corresponding to the general formula (1), to give the phenoxazine ring. The zinc chloride complex compounds which correspond to the general formula (1) and in which Z represents a lower alkoxy group which can be substituted by a cyano group, or represents an acyloxy group, an acylamino group, a lower alkylamino group or a lower dialkylamino group, pass over into the phenoxazine compound with the elimination of this group Z and cyclization. This is effected by treating these compounds of the general formula (1) containing this specifically mentioned group Z, in a suitable protic or aprotic, polar solvent or diluent or mixture thereof, if appropriate by warming, for example at a temperature of about 5° to 120° C., and, if appropriate, in the presence of an acid or a base and/or, if appropriate, in the presence of a compound which precipitates the zinc, linked in the form of a complex, from the compound of the general formula (1) as a sparingly soluble zinc compound, or which converts this zinc into a soluble zinc salt or zincate. If these measures are carried out, cyclization of the quinoneimine compound takes place with elimination of the radical Z to give the phenoxazine compound. Examples of solvents or diluents which can be used for treating the compound of the general formula (1) to effect cyclization are water or aqueous solutions of electrolyte or an organic solvent or diluent. It is preferable to treat the compounds of the general formula (1) in these solvents or diluents by warming, for example at a temperature between 30° and 100° C. It can be advantageous, in this reaction, to add inorganic or organic acids or inorganic or organic basic compounds, including the acid salts or basic salts of inorganic or organic acids, in order to adjust the pH to a value between 2 and 14, preferably 5 and 9. It is advantageous to follow a procedure in which the zinc of the compound of the general formula (1) is precipitated in the form of an insoluble zinc compound or is converted into a soluble zinc compound, such as, for example, into the zincate anion.

Zinc separating agents or zinc precipitants are any agents which form an insoluble compound with the zinc, such as form, in particular, zinc phosphate and zinc carbonate. Examples of compounds which can be used as such precipitants are the alkali metal carbonates or bicarbonates, such as sodium carbonate, potassium carbonate, sodium bicarbonate or potassium bicarbonate, and also ammonium carbonate, calcium carbonate, calcium bicarbonate, magnesium carbonate and also the alkali metal salts of phosphoric acid, such as monosodium, disodium and trisodium phosphate, and the corresponding potassium phosphates and ammonium phosphates, and also the alkali metal and ammonium salts of oxalic acid.

Examples of compounds which convert the zinc into a soluble complex compound are the alkali metal salts of ethylenediaminetetraacetic acid or of nitrilotriacetic acid, ammonia, monoethanolamine, diethanolamine, triethanolamine, ethylenediamine, piperidine and pyridine and also alkaline solutions, such as of an alkali metal hydroxide.

It is particularly advantageous to follow a procedure in which the compounds of the general formula (1) are mixed with water, and an alkali metal carbonate, bicarbonate or phosphate or ammonium carbonate, bicarbonate or phosphate, such as, for example, sodium carbonate, sodium bicarbonate, ammonium carbonate, disodium hydrogen phosphate or diammonium hydrogen phosphate, is added or aqueous solutions of such compounds are mixed with the compounds of the general formula (1). The aqueous suspension or slurry which can be obtained is then warmed. In the course of this the solution begins to take on a deep blue color and the formation of the blue phenoxazine compound is complete after a short time. The water-insoluble zinc compound (carbonate or phosphate) which has been precipitated is filtered off.

The aqueous solution of the phenoxazine thus obtained can be worked up in a customary manner, for example can be converted into the chloride by acidifying with hydrochloric acid to a pH value of 5 to 6. The salt of the phenoxazine compound can then be isolated in a customary manner, for example by spray-drying or by precipitation as a zinc chloride double salt by means of zinc chloride and sodium chloride.

Compounds which correspond to the general formula (1) and in which Z represents a halogen atom, a lower alkyl group, a cyano, carboxylic acid, carbamoyl or sulfamoyl group, a carbamoyl or sulfamoyl group which is monosubstituted or disubstituted by lower alkyl, a trifluoromethyl group or a lower carbalkoxy group, but preferably represents a hydrogen atom, can be converted into the corresponding phenoxazine dyestuffs by oxidative cyclization. Oxidizing agents which are advantageously used for the oxidative cyclization of the these zinc chloride complex compounds corresponding to the general formula (1), which contain a group Z which is different from the removable group Z mentioned above (alkoxy, acyloxy, acylamino or alkylamino), are nitrous acid (for example nitrous acid which has been prepared in the reaction mixture in a manner which is in itself customary by adding sodium nitrite to the acid reaction solution) or peracetic acid. Suitable solvents for this oxidative cyclization are water and organic solvents which are inert towards these oxidizing agents, such as, for example, lower alkanols, such as methanol or ethanol, or acetic acid. The oxidative cyclization is carried out in an acid reaction medium, preferably at a pH value between 2 and 6; the reaction can be carried out at a low temperature, and also at elevated temperature, such as, for example, a temperature between 10° and 80° C. What is necessary in the oxidative cyclization reaction is the presence of a compound capable of removing the zinc which is bound in complex form in the zinc compound of the general formula (1), from this compound, for example by precipitating the zinc as an insoluble compound or by converting the zinc into a soluble compound, such as a soluble complex, by means of a complexing agent. Agents of this type which precipitate zinc or form complexes have already been described previously in the cyclization reaction with the elimination of the group Z.

The phenoxazine compounds which are obtainable in this manner can be worked up and isolated from the reaction mixture of the oxidative cyclization reaction, as described above.

The known phenoxazine compounds thus prepared have the known properties of phenoxazine dyestuffs, but often with a clearer shade. They can be used, in a customary and known manner, as dyestuffs for dyeing the fiber materials which are known for this purpose, particularly polyacrylonitrile fibers, as described in many references in the literature.

The examples below serve to illustrate the invention. The parts are parts by weight and the percentages relate to percentages by weight, unless a note is made to the contrary. Parts by weight and parts by volume are in the relationship of kilogram to liter.

EXAMPLE 1

12.3 parts of 2-amino-4-hydroxytoluene, 16.0 parts of zinc chloride and 19.9 parts of 4-nitroso-3-methoxydiethylaniline in 100 parts by volume of ethanol are stirred under reflux for 2 hours. When no further nitroso compound is detectable by thin layer chromatography, the reaction mixture is cooled and the dark crystalline precipitate is filtered off, washed with 100 parts by volume of ethanol and dried at 60° C. This gives 43.6 parts of a very sparingly soluble, nearly black crystalline powder with a green luster, to which the formula

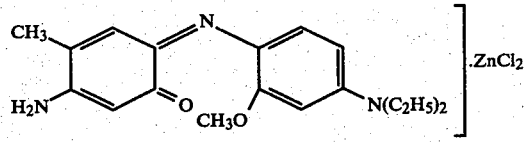

is assigned.

Analysis, calculated on a molecular weight of 449.4 for $C_{18}H_{23}N_3O_2 \cdot ZnCl_2$, gave the following values:

| calculated | | | found: | |
|---|---|---|---|---|
| | C | 48.06%, | | 47.8%, |
| | H | 5.12%, | | 5.3%, |
| | N | 9.35%, | | 9.4%, |
| | O | 7.12%, | | 7.5%, |
| | OCH$_3$ | 6.90%, | | 6.8%, |
| | Zn | 14.55%, | | 14.3%, |
| | Cl | 15.80%, | | 16.0%. |

EXAMPLE 2

The zinc complex compound described in Example 1 can advantageously be prepared without isolating the nitroso compound. The following procedure can be followed in this respect: 179 parts of 3-methoxydiethylaniline are dissolved in a mixture of 600 parts by volume of a saturated, aqueous sodium chloride solution and 232 parts by volume of 30% strength aqueous hydrochloric acid. 139 parts by volume of a 40% strength aqueous sodium nitrite solution are run in slowly at 0° to 5° C., while stirring well; the resulting thick, yellow suspension of the nitrosohydrochloride is stirred further with a distinct excess of nitrite. The excess nitrite is then destroyed with a little amidosulfonic acid. The mixture is rendered alkaline, for example by means of 25% strength aqueous ammonia solution, to a pH value of 9, at 15° to 20° C. 141 parts by volume of a 64% strength aqueous zinc chloride solution are added dropwise, at 15° to 20° C., to this suspension of the nitroso base thus formed, whereupon the orange-colored zinc chloride double salt of the nitroso compound is precipitated in a crystalline form. The pH value is 5.6 to 6.1.

This suspension of crystals is poured into a boiling solution of 123 parts of 2-amino-4-hydroxytoluene in 600 parts by volume of ethanol. The reaction mixture is heated to the boil. The reaction is complete after about 15 minutes. A coarse precipitate of crystals has separated out. The reaction mixture is cooled to 40° C. and filtered and the product is rinsed with about 1,000 parts of cold water. After drying, 436 parts of the compound indicated by the formula in Example 1 are obtained as nearly black crystals with a green luster.

EXAMPLE 3

The procedure followed is as indicated in Example 2, but the 2-amino-4-hydroxytoluene is replaced by 165 parts of 3-diethylaminophenol. This gives 460 parts of a compound to which the formula

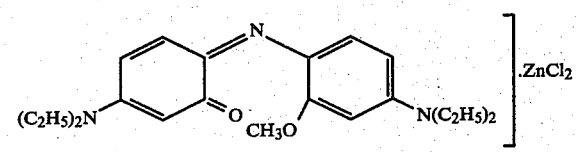

is assigned. It is in the form of nearly black crystals with a green luster.

Analysis (calculated on a molecular weight of 491.3 for $C_{21}H_{29}N_3O_2 \cdot ZnCl_2$):

| calculated: | C | 51.29%, | found: | 51.2%, |
|---|---|---|---|---|
| | H | 5.90%, | | 5.8%, |
| | N | 8.55%, | | 8.6%, |
| | O | 6.51%, | | 6.6%, |
| | OCH$_3$ | 6.31%, | | 6.2%, |
| | Zn | 13.29%, | | 13.2%, |
| | Cl | 14.45%, | | 14.5%. |

EXAMPLE 4

12.3 parts of 2-amino-4-hydroxytoluene, 16.0 parts of zinc chloride and 19.7 parts of 4-nitrosodiphenylamine are stirred in 400 parts by volume of ethanol and the mixture is then heated at the boil for 2 hours. The yellow color of the nitroso compound disappears and a dark precipitate begins to be deposited. The mixture is cooled to 50° C. and the product is filtered off, rinsed with 100 parts by volume of ethanol and dried at 60° C. This gives 42.9 parts of a compound in the form of a nearly black crystalline powder, to which the formula

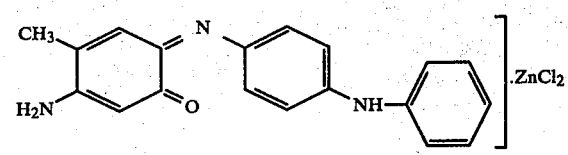

is assigned.

Analysis (calculated on a molecular weight of 439.3 for $C_{19}H_{17}N_3O \cdot ZnCl_2$):

| calculated: | C | 51.90%, | found: | 51.6%, |
|---|---|---|---|---|
| | H | 3.87%, | | 4.0%, |
| | N | 9.56%, | | 9.5%, |
| | O | 3.64%, | | 3.8%, |
| | Zn | 14.86%, | | 14.7%, |
| | Cl | 16.16%, | | 15.8%. |

EXAMPLE 5

16.5 parts of 3-diethylaminophenol, 26 parts of zinc chloride and 17.8 parts of 4-nitrosodiethylaniline in 100 parts by volume of methylglycol are stirred for 2 hours at 80° C. After this time, nitroso compound can no longer be detected by thin layer chromatography. The reaction mixture is cooled to 20° C. and the nearly black precipitate is filtered off, washed with 100 parts by volume of ethanol and dried at 60° C. This gives 45.8 parts of a compound to which the formula

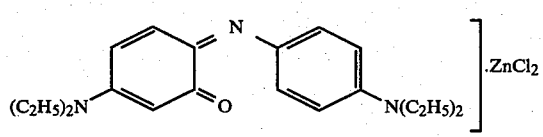

is assigned.

Analysis (calculated on a molecular weight of 461.3 for $C_{20}H_{27}N_3O \cdot ZnCl_2$):

| calculated: | C | 52.03%, | found: | 51.8%, |
|---|---|---|---|---|
| | H | 5.85%, | | 6.0%, |
| | N | 9.10%, | | 9.0%, |
| | O | 3.47%, | | 3.8%, |
| | Zn | 14.16%, | | 13.9%, |
| | Cl | 15.39%, | | 15.5%. |

The zinc chloride complex compound mentioned above is obtained in an almost equally good yield if it is prepared in accordance with the process variant described in Example 2.

EXAMPLE 6

16.5 parts of 3-diethylaminophenol, 16 parts of zinc chloride and 19.2 parts of 4-nitroso-3-methyl-N,N-diethylaniline in 200 parts by volume of methanol are stirred at the boil for 3 hours. The reaction mixture is then cooled and the product which has precipitated is filtered off, washed with 100 parts by volume of methanol and dried. This gives 46.5 parts of a compound to which the formula

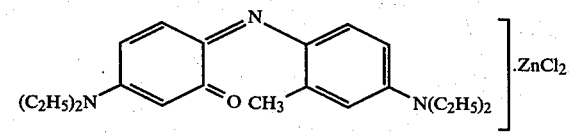

is assigned.

Analysis (calculated on a molecular weight of 475.3 for $C_{21}H_{29}N_3O \cdot ZnCl_2$):

| calculated: | C | 53.02%, | found: | 53.0%, |
|---|---|---|---|---|
| | H | 6.10%, | | 6.4%, |

| | N | 8.84%, | | 8.7%, |
|---|---|---|---|---|
| | O | 3.37%, | | 4.1%, |
| | Zn | 13.74%, | | 13.5%, |
| | Cl | 14.94%, | | 15.0%. |

The new zinc complex compound prepared in this example is obtained in an equally good yield and quality if it is prepared analogously to the process variant described in Example 2.

EXAMPLE 7

If the procedure followed is as described in Example 6 or, analogously, as described in Example 2, but employing, as the starting compounds, 3-hydroxycarbazole and 4-nitroso-3-methoxydiethylaniline or 3-methoxydiethylaniline (for the purpose of introducing the nitroso group), dark crystals of a compound corresponding to the formula

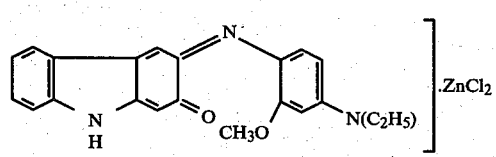

are obtained.

EXAMPLE 8

19.9 parts of 3-hydroxy-4'-methyldiphenylamine, 13.0 parts of zinc chloride and 28.1 parts of 4-nitroso-3-ethoxydiethylaniline in 200 parts by volume of ethylglycol are stirred for 2 hours at 80° C. The reaction is complete after 2 hours. The insoluble precipitate is filtered off, washed with 200 parts by volume of methanol and dried at 60° C. This gives 53 parts of a dark crystalline powder of a compound to which the formula

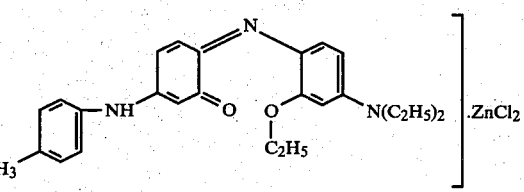

is assigned.

Analysis (calculated on a molecular weight of 539.4 for $C_{25}H_{21}N_3O_2 \cdot ZnCl_2$):

| calculated: | C | 55.62%, | found: | 55.3%, |
|---|---|---|---|---|
| | H | 5.38%, | | 5.8%, |
| | N | 7.79%, | | 7.8%, |
| | O | 5.93%, | | 6.0%, |
| | OC$_2$H$_5$ | 8.34%, | | 8.1%, |
| | Zn | 12.12%, | | 11.8%, |
| | Cl | 13.16%, | | 12.9%. |

This zinc chloride complex compound can be obtained in an equally good yield and purity if it is prepared analogously to the process variant described in Example 2.

EXAMPLE 9

15.8 parts of 2-ethylamino-4-hydroxytoluene, 20.0 parts of zinc chloride and 19.7 parts of 4-nitrosodiphenylamine in 200 parts by volume of ethanol are heated at the boil for 2 hours. The precipitate which has been deposited is filtered off, washed with 100 parts of ethanol and dried. This gives 45.5 parts of a compound in the form of nearly black crystals with a green luster, to which the formula

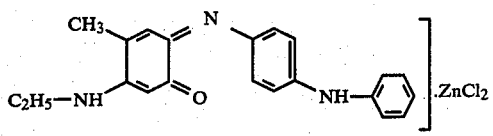

is assigned.

Analysis (calculated on a molecular weight of 467.3 for $C_{21}H_{21}N_3O \cdot ZnCl_2$):

| calculated: | C | 53.93%, | found: | 53.6%, |
|---|---|---|---|---|
| | H | 5.14%, | | 4.6%, |
| | N | 8.99%, | | 8.9%, |
| | O | 3.42%, | | 3.4%, |
| | Zn | 13.97%, | | 14.1%, |
| | Cl | 15.19%, | | 15.5%. |

If the procedure followed is analogous to the procedure described in Example 2, but employing equivalent quantities of 2-ethylamino-4-hydroxytoluene and diphenylamine, the zinc chloride complex compound prepared in this example is obtained in approximately equally good yield and purity.

EXAMPLE 10

19.9 parts of 3-hydroxy-4'-methyldiphenylamine, 26.0 parts of zinc chloride and 13.2 parts of 4-nitroso-3-methoxydiethylaniline in 200 parts by volume of ethanol are stirred at the boil for 2 hours. A dark precipitate is deposited, and this is filtered off after cooling to 60° C.; it is rinsed with 100 parts by volume of ethanol and dried at 60° C. This gives 50 parts of a compound, in the form of dark crystals, to which the formula

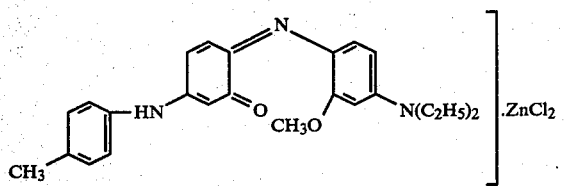

is assigned.

Analysis (calculated on a molecular weight of 525.4 for $C_{24}H_{27}N_3O_2 \cdot ZnCl_2$):

| calculated: | C, | 54.82%, | found: | 54.5%, |
|---|---|---|---|---|
| | H | 5.14%, | | 5.4%, |
| | N | 7.99%, | | 7.8%, |
| | O | 6.09%, | | 6.2%, |
| | OCH$_3$ | 5.9%, | | 5.7%, |
| | Zn | 12.45%, | | 12.2%, |
| | Cl | 13.51%, | | 13.0%. |

The zinc chloride complex compound prepared in this example is obtained in an equally good yield and purity if it is prepared analogously to the procedure described in Example 2.

EXAMPLE 11

16.5 parts of 3-diethylaminophenol, 26.0 parts of zinc chloride and 24.2 parts of 4-nitroso-3-methoxy-4'-methyldiphenylamine in 200 parts by volume of methylglycol are stirred at 80° C. for 2 hours. The reaction mixture is then cooled to 40° C. and the dark precipitate which has been deposited is filtered off, washed with 100 parts by volume of methanol and dried at 60° C. This gives 51.5 parts of a nearly black crystalline powder of the compound corresponding to the formula

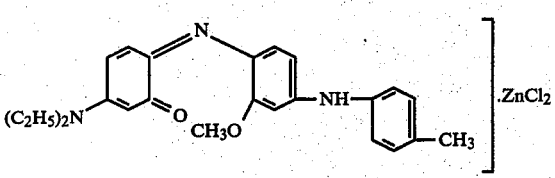

Analysis (calculated on a molecular weight of 525.4 for $C_{24}H_{27}N_3O_2 \cdot ZnCl_2$):

| calculated: | C | 54.82%, | found: | 54.4%, |
|---|---|---|---|---|
| | H | 5.14%, | | 5.3%, |
| | N | 7.99%, | | 8.1%, |
| | O | 6.09%, | | 6.2%, |
| | OCH$_3$ | 5.90%, | | 6.1%, |
| | Zn | 12.45%, | | 12.3%, |
| | Cl | 13.51%, | | 13.5%. |

This zinc chloride complex compound is obtained in approximately the same yield and quality if it is synthesized analogously to the procedure of Example 2.

EXAMPLE 12

16.5 parts of 3-diethylaminophenol, 16.0 parts of zinc chloride and 25.6 parts of 4-nitroso-3-ethoxy-4'-methyldiphenylamine in 200 parts by volume of isopropanol are stirred at the boil for 2 hours. When, after about 2 hours, nitroso compound can no longer be detected by thin layer chromatography, the reaction product which has precipitated is filtered off at 50° C., washed with 200 parts by volume of isopropanol and dried at 60° C. This gives 52.9 parts of a compound in the form of crystals with a greenish luster, to which the formula

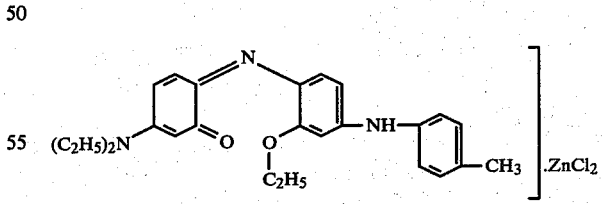

is assigned.

Analysis (calculated on a molecular weight of 539.4 for $C_{25}H_{29}N_3O_2 \cdot ZnCl_2$):

| calculated: | C | 55.62%, | found: | 55.6%, |
|---|---|---|---|---|
| | H | 5.38%, | | 5.3%, |
| | N | 7.79%, | | 7.9%, |
| | O | 5.93%, | | 6.2%, |
| | OC$_2$H$_5$ | 8.34%, | | 8.5%, |
| | Zn | 12.12%, | | 11.9%, |

| | -continued | |
|---|---|---|
| Cl | 13.16%, | 12.9%. |

The procedure analogous to that described in Example 2 is followed, but employing an equivalent quantity of 3-diethylaminophenol and, for the introduction of the nitroso group, an equivalent quantity of 3-ethoxy-4′-methyldiphenylamine. The zinc chloride complex compound prepared in this way corresponds, in yield and purity, to the abovementioned zinc chloride complex compound.

EXAMPLES 13 TO 72

If the procedure, according to the invention, for the preparation of the zinc chloride complex compounds corresponding to the general formula (1) is followed, for example a procedure analogous to the process variants described in the preceding Examples 1 to 12, but using, as the starting compounds, other compounds of formula (2) and formula (3), respectively, another compound of formula (3) and an amine of the general formula

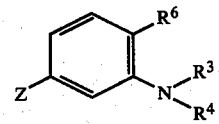

in which $R^3$, $R^4$, $R^6$ an Z have the abovementioned meanings, for the preparation of the nitroso compound, for example using the starting compounds of the tabular examples which follow, characterized by their substituents, the corresponding compounds (1) characterized by the substituents of the formula, are obtained in a good yield, the solid compounds (1) showing the shades indicated in the tabular example.

| Example | Compound (2) $R^1$ | $R^2$ | Compound (1) from $R^5$ | Z | $R^3$ | Compound (3) $R^4$ | $R^6$ | Color of the compound (1) |
|---|---|---|---|---|---|---|---|---|
| 13 | $CH_3$ | $CH_3$ | H | $C_2H_5O$ | $C_2H_5$ | $C_2H_5$ | H | nearly black |
| 14 | $CH_3$ | $C_2H_5$ | $CH_3$ | $CH_3O$ | $C_2H_5$ | $C_2H_5$ | H | " |
| 15 | H | $CH_2CH_2CN$ | $CH_3$ | $CH_3O$ | $C_2H_5$ | $C_2H_5$ | H | " |
| 16 | $CH_3$ | $CH_3$ | H | $CH_3O$ | H | o-Methyl-phenyl | H | " |
| 17 | $C_2H_5$ | $C_2H_5$ | H | $CH_3O$ | H | o-Methyl-phenyl | H | " |
| 18 | $C_2H_5$ | H | $CH_3$ | $CH_3O$ | H | o-Methyl-phenyl | H | " |
| 19 | H | H | $CH_3$ | $C_2H_5O$ | H | o-Methyl-phenyl | H | " |
| 20 | $C_2H_5$ | $C_2H_5$ | H | $CH_3O$ | H | m-Methyl-phenyl | H | " |
| 21 | $CH_3$ | $C_2H_5$ | $CH_3$ | $CH_3O$ | H | Phenyl | H | " |
| 22 | $CH_3$ | $CH_3$ | H | $CH_3O$ | H | p-Methoxy-phenyl | H | " |
| 23 | $C_2H_5$ | $C_2H_5$ | H | $CH_3O$ | H | $CH_2CH_2CN$ | $CH_3O$ | " |
| 24 | H | H | $CH_3$ | $CH_3O$ | H | $CH_2CH_2CN$ | $CH_3O$ | " |
| 25 | $C_2H_5$ | H | $CH_3$ | $C_2H_5O$ | H | $CH_2CH_2CN$ | $C_2H_5O$ | " |
| 26 | $CH_3$ | $CH_3$ | H | $C_2H_5O$ | H | $CH_2CH_2CN$ | H | " |
| 27 | $CH_3$ | $CH_3$ | H | $CH_3O$ | H | p-Ethoxy-phenyl | H | " |
| 28 | $C_2H_5$ | $C_2H_5$ | H | $C_2H_5O$ | H | p-Ethoxy-phenyl | H | " |
| 29 | $C_2H_5$ | $C_2H_5$ | H | H | $CH_3$ | p-Ethoxy-phenyl | H | " |
| 30 | $C_2H_5$ | $C_2H_5$ | H | $CH_3COO$ | $C_2H_5$ | $C_2H_5$ | H | " |
| 31 | $C_2H_5$ | $C_2H_5$ | H | $CH_3CONH$ | $C_2H_5$ | $C_2H_5$ | H | " |
| 32 | $C_2H_5$ | $C_2H_5$ | H | Dimethyl-sulfamoyl | $C_2H_5$ | $C_2H_5$ | H | " |
| 33 | $C_2H_5$ | $C_2H_5$ | H | COOH | $CH_3$ | $CH_3$ | H | " |
| 34 | $C_2H_5$ | $C_2H_5$ | H | Cl | $C_2H_5$ | $C_2H_5$ | H | " |
| 35 | $C_2H_5$ | $C_2H_5$ | H | $CH_3CONH$ | $CH_2CH_2OH$ | $CH_2CH_2OH$ | $CH_3O$ | " |
| 36 | $C_2H_5$ | $C_2H_5$ | H | $CH_3CONH$ | $CH_2CH_2OH$ | $CH_2CH_2CN$ | $CH_3O$ | " |
| 37 | H | $C_2H_5$ | H | $CH_3COO$ | $C_2H_5$ | $C_2H_5$ | H | " |
| 38 | H | H | $CH_3$ | $CH_3CONH$ | $CH_2CH_2OH$ | $CH_2CH_2OH$ | $CH_3O$ | " |
| 39 | $C_2H_5$ | $C_2H_5$ | H | $CH_3$ | $CH_3COOCH_2CH_2-$ | $CH_3COOCH_2CH_2-$ | H | " |
| 40 | H | $C_2H_5$ | H | Cl | $CH_2CH_2OH$ | $CH_2CH_2OH$ | H | " |
| 41 | H | $C_2H_5$ | $CH_3$ | $CH_3O$ | H | o-Methoxy-phenyl | H | " |
| 42 | H | $C_2H_5$ | $CH_3$ | $CH_3O$ | H | o-Ethoxy-phenyl | H | " |
| 43 | H | $C_2H_5$ | $CH_3$ | $CH_3O$ | H | p-Chloro-phenyl | H | " |
| 44 | H | H | $CH_3$ | $CH_3O$ | H | o-Methyl-phenyl | H | " |
| 45 | $CH_3$ | $C_2H_5$ | $CH_3$ | $CH_3O$ | H | o-Methyl-phenyl | H | " |
| 46 | H | H | $CH_3$ | $CH_3COO$ | $C_2H_5$ | $C_2H_5$ | H | " |
| 47 | $C_2H_5$ | $C_2H_5$ | H | H | $C_2H_5$ | $CH_2CH_2CONH_2$ | H | " |
| 48 | H | Phenyl | H | $CH_3O$ | H | Phenyl | H | " |
| 49 | $C_2H_5$ | $C_2H_5$ | H | $CN-CH_2-O-$ | $C_2H_5$ | $C_2H_5$ | H | " |
| 50 | H | o-Ethoxy-phenyl | H | $CH_3O$ | $C_2H_5$ | $C_2H_5$ | H | " |

-continued

| Example | Compound (2) R¹ | R² | R⁵ | Compound (1) from Z | R³ | Compound (3) R⁴ | R⁶ | Color of the compound (1) |
|---|---|---|---|---|---|---|---|---|
| 51 | H | o-Ethoxyphenyl | H | $C_2H_5O$ | $C_2H_5$ | $C_2H_5$ | H | " |
| 52 | $C_2H_5$ | $C_2H_5$ | H | $CH_3O$ | H | o-Ethoxyphenyl | H | " |
| 53 | $C_2H_5$ | $C_2H_5$ | H | $C_2H_5O$ | H | o-Ethoxyphenyl | H | " |
| 54 | H | o-Ethoxyphenyl | H | $CH_3COO$ | $C_2H_5$ | $C_2H_5$ | H | " |
| 55 | H | H | H | $CH_3O$ | $C_2H_5$ | $C_2H_5$ | H | " |
| 56 | H | H | $CH_3$ | $C_2H_5O$ | $C_2H_5$ | $C_2H_5$ | H | " |
| 57 | H | $C_2H_5$ | $CH_3$ | $CH_3O$ | $C_2H_5$ | $C_2H_5$ | H | " |
| 58 | H | $C_2H_5$ | $CH_3$ | $C_2H_5O$ | $C_2H_5$ | $C_2H_5$ | H | " |
| 59 | $C_2H_5$ | $C_2H_5$ | H | $C_2H_5O$ | $C_2H_5$ | $C_2H_5$ | H | " |
| 60 | H | Phenyl | H | $C_2H_5O$ | $C_2H_5$ | $C_2H_5$ | H | " |
| 61 | H | Phenyl | H | $CH_3O$ | $C_2H_5$ | $C_2H_5$ | H | " |
| 62 | H | Phenyl | H | $CH_3COO$ | $C_2H_5$ | $C_2H_5$ | H | " |
| 63 | $C_2H_5$ | $C_2H_5$ | H | $CH_3O$ | H | Phenyl | H | " |
| 64 | $C_2H_5$ | $C_2H_5$ | H | $C_2H_5O$ | H | Phenyl | H | " |
| 65 | $C_2H_5$ | $C_2H_5$ | H | $CH_3O$ | H | 2,5-Dimethylphenyl | H | " |
| 66 | $C_2H_5$ | $C_2H_5$ | H | $C_2H_5O$ | H | 2,5-Dimethylphenyl | H | " |
| 67 | H | 2,5-Dimethylphenyl | H | $CH_3O$ | $C_2H_5$ | $C_2H_5$ | H | " |
| 68 | H | 2,5-Dimethylphenyl | H | $C_2H_5O$ | $C_2H_5$ | $C_2H_5$ | H | " |
| 69 | H | 2,5-Dimethylphenyl | H | $CH_3COO$ | $C_2H_5$ | $C_2H_5$ | H | " |
| 70 | H | p-Methoxyphenyl | H | $CH_3O$ | $C_2H_5$ | $C_2H_5$ | H | " |
| 71 | H | $C_2H_5$ | $CH_3$ | $C_2H_5O$ | H | o-Methylphenyl | H | " |
| 72 | H | p-Methylphenyl | H | $CH_3COO$ | $C_2H_5$ | $C_2H_5$ | H | " |

EXAMPLE 73

27.8 parts of the zinc chloride complex compound of Example 50 are suspended in 100 parts by volume of N-methylpyrrolidone. The mixture is warmed to 40° C. and stirred at this temperature for about 8 hours. A deep blue solution is formed. When only the clear blue spots of the phenoxazine dyestuff to be formed can be seen by means of thin layer chromatography, a small quantity of impurity is filtered off to give a ready-to-use solution of the chloride or chlorozincate of the dyestuff cation of the formula

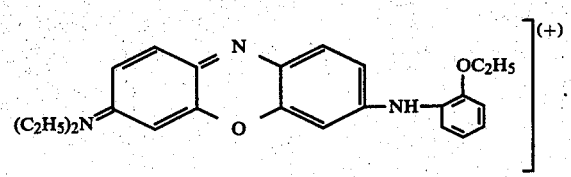

If it is desired to isolate a zinc-free material, the blue solution is added dropwise to a mixture of 500 parts by volume of water and 8 parts of diammonium hydrogen phosphate and the precipitated zinc phosphate is filtered off after about one hour. 5 parts of 5 N hydrochloric acid are added and the dyestuff chloride is salted out with 50 parts of sodium chloride. Polyacrylonitrile fiber material can be dyed with these phenoxazine dyestuff salts in a customary manner in clear blue, intense and fast shades.

The same dyestuff is obtained if, with an otherwise identical procedure, the zinc chloride complex compounds of Examples 51, 52, 53 or 54 are employed.

EXAMPLE 74

An aqueous alkaline solution having a pH value of 9 is prepared using 23.1 parts of 85% strength aqueous phosphoric acid and about 48 parts of 33% strength sodium hydroxide solution in 300 parts of water. 87.1 parts of the zinc chloride complex compound of Example 55 are added to this solution at about 20° C. and this suspension is stirred for about 12 hours at 20° C. The pH has then fallen to a value of about 6.7. The reaction mixture is warmed to 40° C. and stirred for a further 2 hours, in the course of which the pH falls to a value of about 6.1. The mixture is then warmed to 60° C. and stirred for 3 hours at this temperature, after which a pH value of 4.9 is obtained. Only a clear blue spot can then be seen in a sample taken for thin layer chromatography, together with a trace of an impurity. The mixture is filtered and the zinc phosphate residue is rinsed in portions with 300 parts of water at 60° C. The chlorozincate of the dyestuff of the formula

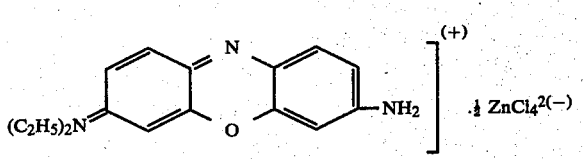

is precipitated from the clear, blue dyestuff solution by means of 15 parts of zinc chloride and 100 parts of sodium chloride, and is filtered off and dried at 60° C. This gives 74 parts of a dyestuff powder which is very readily soluble in water.

A zinc-free dyestuff solution can be obtained in a customary manner by precipitating the zinc in the form of phosphate.

EXAMPLE 75

89.9 parts of the zinc chloride complex compound of the formula indicated in Example 1, which has been prepared in accordance with Example 1 or Example 2, are suspended in 200 parts of water at 60° C. and 24 parts of sodium bicarbonate are added in portions in the course of about 2 hours. The reaction mixture turns a deep blue color; it is stirred for about a further 3 hours at 60° C., in the course of which the pH falls to a value of about 7. The zinc carbonate is filtered off and washed with water at 60° C.; this gives a clear, dark blue solution of the dyestuff of the formula

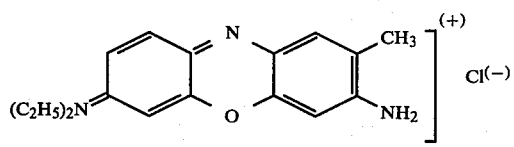

which produces a ready-to-use liquid formulation if the pH is adjusted to a value of 4.5 with glacial acetic acid. The yield in the cyclization reaction to form the phenoxazine is quantitative, as can be determined by measuring the depth of color colorimetrically.

The dyestuff can be converted into the tetrachlorozincate in a customary manner by means of an aqueous solution of zinc chloride and sodium chloride and can be precipitated quantitatively in coarse crystals having a green sheen. It is very readily soluble in water and dilute acetic acid and dyes polyacrylonitrile fiber material from an acid bath in a customary manner in strong, clear blue shades which have good fastness properties.

EXAMPLE 76

92.6 parts of the zinc chloride complex compound of Example 56 are suspended in 250 parts of water at 60° C. 30 parts of diammonium hydrogenophosphate are sprinkled in within the course of 3 hours, while stirring well. The mixture is stirred for a further 3 hours at 60° C. and the resulting deep blue solution, which has a pH value of 6 to 6.4, is then filtered to free it from zinc phosphate; the latter can be rinsed with 250 parts of water at 60° C. This gives a ready-to-use liquid formulation of the dyestuff chloride indicated by the formula in Example 75. Colorimetric determination of the depth of color shows that the cyclization reaction to form the phenoxazine has taken place virtually quantitatively. The zinc content of this dyestuff solution is below 10 ppm, so that the dyestuff can also be used in cases where the commercially available tetrachlorozincates cannot be used. The dyestuff chloride, mixed with a small quantity of ammonium chloride, can be obtained in a quantitative yield from this dyestuff solution in a customary manner in well-crystallized crystals with a green luster, by spray-drying. It is very readily soluble in water and also in lower alcohols, such as methanol and ethanol, in ethylene glycol, in acid amides, such as dimethylformamide or N-methylpyrrolidone, or in aliphatic carboxylic acids, such as formic acid, acetic acid or propionic acid.

As in the case of the dyestuff salt prepared in accordance with Example 75, the phenoxazine dyestuff prepared in this example can be used to dye polyacrylonitrile fiber materials in a customary manner in clear blue shades which have a good depth of color.

EXAMPLE 77

95.5 parts of the zinc chloride complex compound of Example 57 are suspended in 300 parts of water at 60° C. 25 parts of ammonium carbonate are introduced in portions in the course of about 3 hours. Stirring is continued for a further 3 hours at 60° C. After this, only the phenoxazine compound which has been formed can be detected, together with a trace of an impurity, in the reaction mixture by thin layer chromatography. The zinc carbonate is filtered off and washed with 250 parts of water at 60° C.; this gives a clear blue filtrate which has a pH value of 7.5. The pH is adjusted to a value of 5.8 with glacial acetic acid. This gives a ready-to-use solution of the phenoxazine dyestuff of the formula

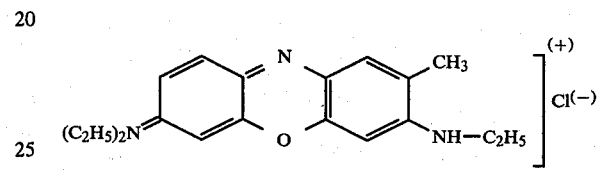

with which polyacrylonitrile fiber materials can be dyed in a customary manner in clear blue, intense shades which have good fastness properties. Colorimetric determination of the depth of color of the filtrate obtained shows that the cyclization reaction has taken place virtually quantitatively.

EXAMPLE 77a

The procedure followed is as described in Example 77, but 97 parts of the zinc chloride complex compound of Example 58 are used as the starting material. The phenoxazine dyestuff is obtained in the same high yield and quality.

EXAMPLE 78

94 parts of the zinc chloride complex compound of Example 3 are added, at 20° C., to a solution which has a pH value of 9 and is composed of 23.1 parts of 85% strength aqueous phosphoric acid, about 48 parts of 33% strength sodium hydroxide solution and 300 parts of water. The mixture is stirred for 12 hours, in the course of which the pH falls to a value of 7.8. The temperature is then raised to 40° C.; the reaction solution is stirred for a further 2 hours, after which it exhibits a pH value of 7.3. It is then stirred for a further 3 hours at 60° C. until it has a pH of 6 to 6.4. This gives a deep blue solution of the phenoxazine compound, which is formed in quantitative yield. The zinc phosphate is filtered off. The zinc content of the filtrate is below 10 ppm. The dyestuff chloride corresponding to the formula

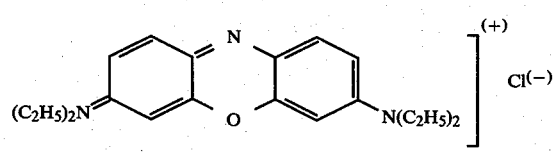

can be obtained in a customary manner by spray-drying. The solution can also be converted in a customary manner, by means of sodium fluoborate, into the dyestuff tetrafluoborate, which is very well crystallized.

These dyestuff salts obtained from the zinc chloride complex compound of Example 3 dye polyacrylonitrile fiber materials in clear blue shades which have good depth of color and good fastness properties.

EXAMPLE 79

96 parts of the zinc chloride complex compound of Example 59 are added, at 20° C., to an alkaline sodium phosphate solution such as is described at the beginning of Example 78, and the mixture is stirred, first for 12 hours at 20° C., then for 2 hours at 40° C. and then for a further 3 hours at 60° C. This gives a dark blue solution which has a pH value of 6.5 and contains the phenoxazine compound, which has been formed in a quantitative yield. The zinc phosphate is filtered off and washed with 200 parts of water at 60° C., 12 parts of a 65% strength aqueous zinc chloride solution are added to the filtrate and the dyestuff salt is precipitated completely by means of about 100 parts of sodium chloride. This gives the tetrachlorozincate of the phenoxazine dyestuff indicated in Example 78. With this dyestuff also clear blue dyeings which have a good depth of color can be obtained on polyacrylonitrile fiber material.

EXAMPLE 80

About 239 parts of an 33% aqueous sodium hydroxide solution are added slowly to a solution of 115.5 parts of an 85% strength aqueous phosphoric acid in 1500 parts of water to give an alkaline aqueous solution which has a pH value of 9. 491 parts of the zinc chloride complex compound of Example 3 are introduced at a temperature of 20° C., together with 50 parts of kieselguhr, and the reaction mixture is stirred for 12 hours at 20° C., for 2 hours at 40° C. and finally for three hours at 60° C. A deep blue solution which has a pH value of 6.3 is obtained. Only a clear blue spot can be detected by thin layer chromatography. The mixture is filtered and the residue is rinsed with 1000 parts of water at 60° C., to give a deep blue clear solution of dyestuff which, according to colorimetric measurement of the depth of color, contains, in a virtually quantitative yield, the phenoxazine chloride corresponding to the formula indicated in Example 78. The dyestuff salt can be isolated by evaporating the solution. This gives about 520 parts of residue. The dyestuff salt can be dissolved in 300 parts of ethylene glycol, leaving 38 parts of sodium chloride, which is filtered off. A concentrated solution in ethylene glycol of the phenoxazine chloride compound indicated by the formula in Example 78 is obtained in this way, which can be used in a conventional manner to prepare dyebaths in which polyacrylonitrile fiber material can be dyed with a good depth of color in clear, greenish-tinged blue shades.

EXAMPLE 81

26 parts of the zinc chloride complex compound of Example 60 are suspended in a mixture of 300 parts of water and 400 parts by volume of toluene. 100 parts by volume of an aqueous 5 N sodium hydroxide solution are added dropwise in the course of one hour and the mixture is then stirred for 2 hours at 50° C. The toluene layer turns an intense claret color, whilst the aqueous phase becomes nearly colorless. The aqueous phase is separated off, the toluene phase is washed twice more with, in each case, 100 parts of water, and the toluene is then removed by steam distillation. After cooling, 17 parts of crystals, with a green luster, of the anhydro-base of the formula

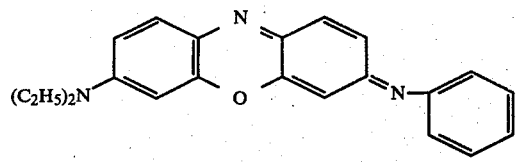

are obtained. This base dissolves in acids to form the greenish-tinged blue phenoxazine salt, which, using customary dyeing methods, dyes polyacrylonitrile fiber materials in intense shades of a clear, greenish-tinged blue color.

The anhydro-base prepared in this Example can be obtained in the same manner if the zinc chloride complex compound of Example 61, 62, 63 or 64 are used as the starting compound and if the procedure indicated here is employed.

EXAMPLE 82

27 parts of the zinc chloride complex compound of Example 65 are stirred in 100 parts of water at 30° C. 50 parts by volume of a 25% strength aqueous ammonia solution are added in the course of 1 hour and the mixture is stirred, first for 2 hours at 30° C. and then for a further 5 hours at 50° C. The mixture is allowed to cool and the dark precipitate is filtered off, washed with water until it is neutral and dried at 60° C. This gives 18.5 parts of dark crystals, with a green luster, of the anhydro-base of the formula

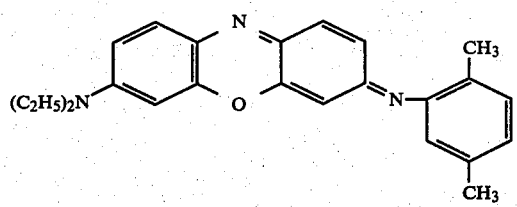

which is a single substance according to thin layer chromatography. With acids, it gives the phenoxazine dyestuff salt, which can be employed in a customary manner for dyeing polyacrylonitrile fiber materials and dyes these materials in clear, greenish-tinged blue shades.

The anhydro-base prepared in this example can be obtained in the same quality and yield by the procedure indicated if the zinc chloride complex compound of Example 66, 67, 68 or 69 is used as the starting compound.

EXAMPLE 83

50.9 parts of the zinc chloride complex compound of Example 7 are suspended in 150 parts by volume of dimethylformamide. The mixture is stirred for 8 to 10 hours at 40° C. and then for a further 12 hours at 20° C. Thin layer chromatography shows that the resulting deep blue solution contains the resulting clear blue phenoxazine compound as well as a small quantity of impurity and a little of the starting material. 500 parts of water and 300 parts by volume of a 5 N hydrochloric acid are added to this reaction solution and the mixture is heated to 80° C. and filtered and the residue is rinsed with about 1,000 parts of water. The chlorozincate salt of the phenoxazine dyestuff is precipitated by means of 12 parts by volume of a 65% strength aqueous zinc chloride solution and 100 parts of sodium chloride. It is filtered off and dried at 60° C. 40 parts of dyestuff of the formula

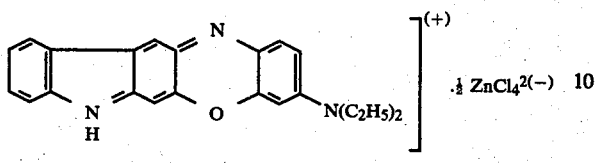

are obtained in the form of nearly black crystals. Polyacrylonitrile fiber materials can be dyed with the dyestuff in a known manner, and intense, violet-blue dyeings which have good fastness properties are obtained.

This dyestuff cn be obtained in the same yield and quality by the procedure indicated if 52 parts of the zinc chloride complex compound of the formula

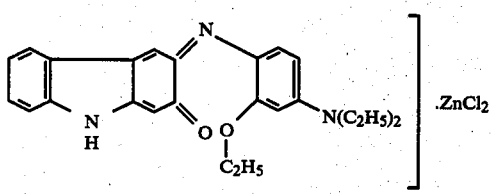

are used as the starting material.

EXAMPLE 84

27 parts of the zinc chloride complex compound of Example 70 are suspended in 200 parts by volume of ethanol. 40 parts by volume of a 5 N aqueous sodium hydroxide solution are added at 25° C. in the course of one hour. The solution turns a red-violet color and a pale precipitate composed of sodium chloride and zinc hydroxide begins to be deposited. The mixture is stirred for a further 12 hours at 25° C. and is filtered and a mixture composed of 500 parts of water, 50 parts by volume of a 5 N hydrochloric acid and 50 parts of sodium chloride is added dropwise to the filtrate, whilst stirring well. The precipitate is filtered off and dried. 20.5 parts of the compound of the formula

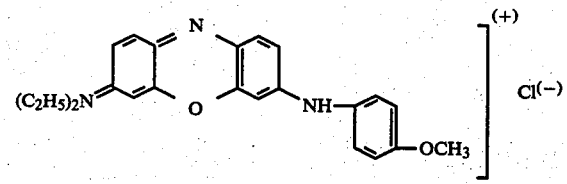

are obtained in the form of dark crystals having a green sheen. This phenoxazine dyestuff dyes polyacrylonitrile fiber materials in a known manner in deep clear greenish-tinged blue shades which have very good fastness to light.

EXAMPLE 85

25.5 parts of the zinc chloride complex compound of Example 18 are stirred in 150 parts of a 10% strength aqueous ammonia solution for 20 hours at 60° C. The mixture is then filtered and the residue is washed with 200 parts of water until it is neutral, and is dried at 60° C. 16.9 parts of the compound of the formula

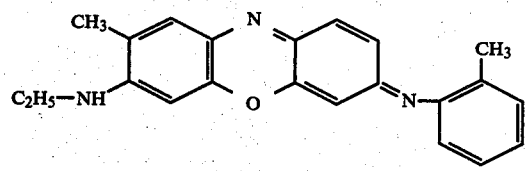

are obtained in the form of a dark crystalline powder. This anhydro-base is virtually free from zinc. It dissolves in acids to form the blue phenoxazine dyestuff salt, which dyes polyacrylonitrile fiber materials by known dyeing methods in clear blue, intense shades. The phenoxazine dyestuff is obtained in the same quality and yield by the procedure described here, if the zinc chloride complex compound of Example 71 is used as the starting material.

EXAMPLE 86

26.2 parts of the zinc chloride complex compound of Example 10 are suspended in 100 parts of water. 75 parts of triethanolamine are added in the course of 30 minutes and the mixture is stirred for a further 20 hours at 50° C. The product is filtered off and washed with water until it is neutral. After the substance has been dried, 17 parts of the zinc-free anhydro-base of the formula

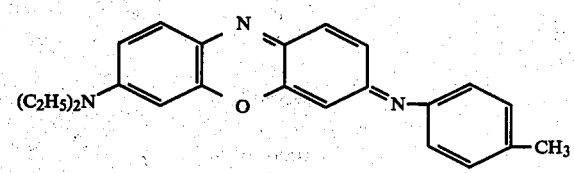

are obtained in the form of dark crystals having a green sheen. With acids, this anhydro-base gives the blue phenoxazine dyestuff salt, which dyes polyacrylonitrile fiber materials by a customary dyeing procedure in clear blue shades which have good fastness properties and good depth of color.

This dyestuff is obtained in the same quality and yield if the same procedure as described here is followed for the preparation of the phenoxazine dyestuff, but using the zinc chloride complex compound of Example 8, 11, 12 or 72 as the zinc chloride complex compound.

EXAMPLE 87

25 parts of the zinc chloride complex compound of Example 7 are stirred in 150 parts of N-methylpyrrolidone for 15 hours at a temperature of 60° C. The resulting deep blue solution is filtered to free it from a small quantity of an insoluble residue, which is rinsed with 50 parts by volume of N-methylpyrrolidone. The filtrate is stirred into a solution of 8 parts of diammonium hydrogenophosphate in 1,000 parts of water. The precipitate is filtered off at 50° C. and is rinsed with 200 parts of water at 50° C. 5 parts by volume of an aqueous 5 N hydrochloric acid, followed by 100 parts of sodium chloride, are added to the filtrate thus obtained. The precipitated dyestuff is filtered off and dried at 60° C. 15 parts of the dyestuff salt corresponding to the formula indicated in Example 83 are obtained in the form of the chloride. It also dyes polyacrylonitrile fiber materials in deep, violet-blue shades which have good fastness properties.

EXAMPLE 88

11.5 parts of the zinc chloride complex compound of Example 5 are suspended in 200 parts by volume of ethanol and 10 parts by volume of glacial acetic acid and the mixture is heated to a temperature of 70° C. A solution of 3.75 parts of the sodium salt of ethylenediaminetetraacetic acid in 20 parts of water, the pH of which has been adjusted to a value of 7 with glacial acetic acid, is added. 2.3 parts of solid sodium nitrite are then added to the whole mixture in the course of about 5 minutes and the reaction mixture is stirred for 8 hours at 70° C. A dark blue solution of the phenoxazine dyestuff of the formula

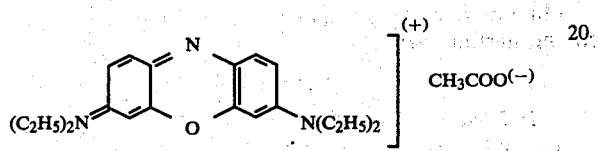

is obtained, which can be worked up in a customary manner, as described in the preceding examples.

EXAMPLE 89

11.5 parts of the zinc chloride complex compound described in Example 5 are suspended, analogously to Example 88, in 200 parts by volume of ethanol and 10 parts by volume of glacial acetic acid. An aqueous solution, having a pH value of 7, of 3.75 parts of the sodium salt of ethylenediaminetetraacetic acid in water is added at 70° C. and 4.8 parts of a 40% strength aqueous solution of peracetic acid are then added dropwise in the course of about 5 minutes. This reaction mixture is stirred for a further 8 hours at 70° C. and a dark blue solution of the phenoxazine dyestuff, which can be worked up in a customary manner, is obtained.

We claim:

1. A zinc chloride complex compound corresponding to the general formula (1)

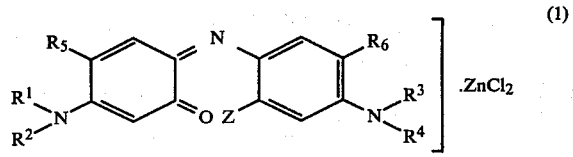

wherein:
R$^1$ is hydrogen or lower alkyl unsubstituted or substituted by chlorine, hydroxy, lower alkoxy, cyano, lower alkanoyloxy, carbamoyl or phenyl,
R$^2$ is hydrogen or lower alkyl unsubstituted or substituted by chlorine, hydroxy, lower alkoxy, cyano, lower alkanoyloxy, carbamoyl or phenyl, or is phenyl unsubstituted or substituted by substituents belonging to the group comprising chlorine, lower alkyl, lower alkoxy, carbamoyl, sulfamoyl, carbamoyl monosubstituted or disubstituted by lower alkyl, and sulfamoyl monosubstituted or disubstituted by lower alkyl,
R$^3$ is hydrogen or lower alkyl unsubstituted or substituted by chlorine, hydroxy, lower alkoxy, cyano, lower alkanoyloxy, carbamoyl or phenyl,
R$^4$ is hydrogen, lower alkyl unsubstituted or substituted by chlorine, hydroxy, lower alkoxy, cyano, lower alkanoyloxy, carbamoyl or phenyl, or is phenyl unsubstituted or substituted by substituents belonging to the group comprising chlorine, lower alkyl, lower alkoxy, carbamoyl, sulfamoyl, carbamoyl monosubstituted or disubstituted by lower alkyl, and sulfamoyl monosubstituted or disubstituted by lower alkyl,
R$^5$ is hydrogen, halogen, lower alkyl or lower alkoxy, or
R$^1$ and R$^5$ together form the o-phenylene,
R$^6$ is hydrogen, halogen, lower alkyl or lower alkoxy,
Z is lower alkoxy or lower alkoxy substituted by cyano, or is acyloxy, acylamino, lower alkylamino or lower dialkylamino.

* * * * *